United States Patent [19]

Dror

[11] 4,198,967
[45] Apr. 22, 1980

[54] TONGUE HOLDER

[76] Inventor: Leon L. Dror, 15641 N. 21st St., Phoenix, Ariz. 85022

[21] Appl. No.: 869,306

[22] Filed: Jan. 13, 1978

[51] Int. Cl.² ............................................. A61M 15/00
[52] U.S. Cl. ................................. 128/136; 128/207.14
[58] Field of Search .............. 128/136, 346, 137, 321, 128/140 R, 354, DIG. 26, 173.3, 185, 205, 206, 207, 208, 12, 13, 14, 15, 19, 223, 145.5, 222, 147

[56] References Cited

U.S. PATENT DOCUMENTS

| 625,879 | 5/1899 | Gardner | 128/137 |
| 2,521,084 | 9/1950 | Oberto | 128/136 |
| 3,513,835 | 5/1970 | De Ceuster | 128/12 |
| 3,616,497 | 11/1971 | Esposito | 128/346 X |
| 3,809,094 | 5/1974 | Cook | 128/321 |
| 4,112,951 | 9/1978 | Hulka et al. | 128/346 |

FOREIGN PATENT DOCUMENTS

| 81221 | 12/1919 | Fed. Rep. of Germany | 128/346 |
| 679941 | 7/1939 | Fed. Rep. of Germany | 128/346 |

OTHER PUBLICATIONS

Lieberman, Leo, M.D. et al. "A New Tongue-Holding Airway" *Illinois Medical Journal* Jan. 1952, pp. 39, 40 (no further information submitted).

*Primary Examiner*—Edgar S. Burr
*Assistant Examiner*—James R. Feyrer
*Attorney, Agent, or Firm*—Cahill, Sutton & Thomas

[57] ABSTRACT

A tongue holding device incorporating an upper and lower clamp arms each terminating at the distal end thereof in an upper and lower clamp for contacting, grasping and holding the tongue of an unconscious person during the procedure of resuscitation and artificial respiration. An upper and lower stop each extend from a different one of the clamp arms for contacting the outside of the person's mouth in order to limit the distance the apparatus may be dragged by the clamped tongue into the mouth. A U-shaped spring contacts the outer surface of each of the clamp arms to urge the arms, and therefore the clamps, toward one another to grasp and hold the tongue therebetween. A tubular extension is formed integrally with the U-shaped spring to permit the attachment of a hose for supply of air, oxygen and/or other gases to the unconscious person.

4 Claims, 8 Drawing Figures

TONGUE HOLDER

The present invention pertains to devices to overcome the difficulty of a receding tongue in a semi-conscious, or an unconscious person; more particularly, the present invention relates to a device for grasping and holding the tongue and in that way preventing the tongue from sliding back into the pharynx, obstructing the trachea, and making completely impossible the process of breathing, particularly the inhalation phase.

When artificial respiration is being administered, the presently accepted technique is the well known mouth-to-mouth respiration. However, an unconscious person's tongue, due to its own gravity, recedes into the person's throat (as a result of relaxation of the muscles supporting the tongue) blocking the trachea and not only interfering, but frequently rendering impossible the administration of artificial respiration.

This difficulty caused by the receding tongue in unconscious patients is usually overcome during general anesthesia for surgical procedures by the use of a rigid curved tube, the so-called oro-pharyngeal airway which is inserted into the patient's pharynx to provide unobstructed ventilation of the lungs; that is, to insure free passage to and from the lungs of air, oxygen and anesthetic gases.

Many surgical procedures require light, or even very light anesthesia in view of the specific kind of the treatment involved, the time required for the procedure, etc.; however, because of the reflex activity of the patient and the necessary use of an airway to prevent the tongue from blocking the trachea, it is presently common practice to induce a far deeper stage of anesthesia than it may actually be needed for the procedure.

It is universally recognized that this instrument (the oro-pharyngeal airway) is inadequate because its induction and presence in a person's throat causes reflectively retching and gagging unless the person is in deep anesthesia. Even when such deep anesthesia is utilized for the surgical procedure, the danger from the reflex activity nevertheless exists and therefore great care by highly trained medical personnel is always an absolute necessity during the recovery from general anesthesia and regaining of consciousness, which often takes a considerable length of time.

It is obvious that a device which could make possible the avoidance of using deep stages of general anesthesia wherever applicable would be of great benefit to patients and would also have a considerable economic effect by shortening and simplifying the post-anesthetic care in the recovery rooms of all surgical institutions.

It is therefore an object of the present invention to provide apparatus for grasping and holding the tongue to prevent the tongue from obstructing the trachea.

It is also an object of the present invention to provide an apparatus for grasping and holding the tongue which apparatus contacts the outside of a patient's mouth to limit the distance that the apparatus can be pulled by the clamped tongue into the mouth to thereby prevent the back of the tongue from obstructing the trachea.

It is still another object of the present invention to provide an inexpensive and readily used device for clamping a person's tongue to prevent the tongue from blocking the trachea while nevertheless permitting mouth-to-mouth respiration.

It is still another object of the present invention to provide an apparatus for grasping and holding a person's tongue in order to prevent the tongue from blocking the trachea when the person is unconscious and which provides a convenient means for connection to a hose for administration of air, or oxygen or other gases to the unconscious person during the procedure of resuscitation.

These and other objects of the present invention will become apparent to those skilled in the art as the description thereof proceeds.

Briefly, in accordance with the embodiment chosen for illustration, a device for clamping a person's tongue is formed with an upper and a lower clamping arm each of which terminates at the distal end thereof in a clamp for contacting and grasping the tongue. The clamps are formed with an indented portion to thereby avoid contact with the frenulum of the tongue. A U-shaped spring contacts each of the clamping arms and urges the arms toward one another to therefore provide the clamping force to the respective clamps. A tubular extension is formed integrally with the U-shaped clamp to provide a means for attachment to a hose for the supply of air, oxygen and/or other gases.

The arms are held in rocking contact with each other along a fulcrum and are each provided with extensions at the proximal ends thereof forming an upper and lower grip that may be grasped between the thumb and forefinger to force the clamping arms apart. An upper and a lower stop are formed integrally with the upper and lower clamping arms respectively; the stops extend substantially transversely of the respective arms for contacting the outside of the patient's mouth to limit the distance that the apparatus may be pulled into the mouth. The apparatus is inexpensively and ruggedly formed of suitable rigid plastic materials and, in the embodiment chosen for illustration, are formed of three individual plastic pieces, two of which are identical to thereby provide an extremely inexpensive structure which can be rendered either re-useable through sterilization or are sufficiently inexpensive to be disposable.

The present invention may more readily be described by reference to the accompanying drawings in which.

Figure 1:
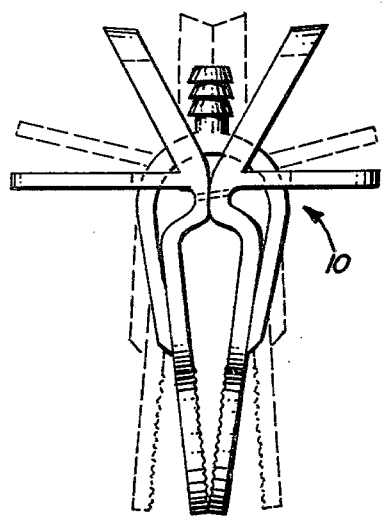
FIG. 1 is a top view of apparatus constructed in accordance with the teachings of the present invention showing the device in its unexpanded state and showing, in broken lines, the device in an expanded state as it would appear prior to insertion into a patient's mouth to grasp the patient's tongue.
Figure 2:
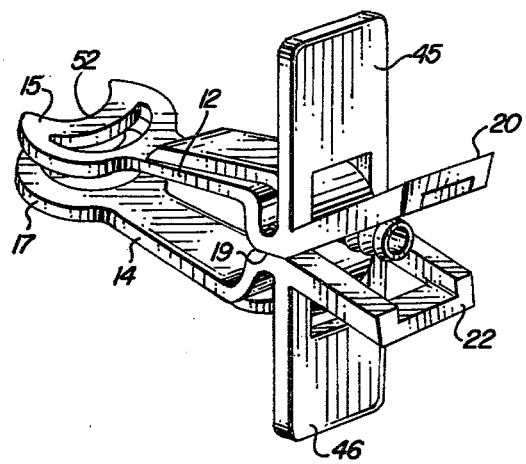
FIG. 2 is a perspective view of the device of FIG. 1.

Referring now to the drawings, a device constructed in accordance with the teachings of the present invention is shown generally at 10 and incorporates an upper clamping arm 12 and a lower clamping arm 14. An upper clamp 15 and a lower clamp 17 are formed integrally with the upper clamping arm 12 and the lower clamping arm 14, respectively, at the forward or distal ends thereof. The clamping arms 12 and 14 extend rearwardly from the clamps 15 and 17 and are formed so as to provide a fulcrum 19 for rocking motion therebetween. The arms are further extended rearwardly of the upper and lower clamp 15 and 17 and rearwardly of the fulcrum 19 to form an upper grip 20 and a lower grip 22, respectively. Thus, when the upper and lower grips are grasped between the thumb and forefinger and are pressed toward one another, the upper and lower clamping arms 12 and 14 are swung away from each other about the fulcrum 19.

The upper and lower clamping arms 12 and 14 may be prevented from relative sliding motion with respect to each other in any convenient manner; however, in the embodiment chosen for illustration, the two arms are "staked" through the utilization of two pivot pins 25 and 26. The clamping arms 12 and 14 are urged toward one another through the use of a U-shaped spring member 30 which may be made of the same molded plastic material as the clamping arms. The plastic material usually has sufficient resilience to permit the respective arms 31 and 32 of the spring to be slightly forced apart without causing a permanent set in the plastic. Pins 34 and 35 are molded integrally with the arms 31 and 32, respectively, and extend into corresponding holes, such as that shown at 38, in the respective clamping arms to maintain the spring 30 in place.

A tubular extension 37 is also molded integrally with the spring 30 and provides a convenient means for attachment of a hose 40 to the apparatus while providing an unobstructed passage into the person's mouth.

Figure 3:
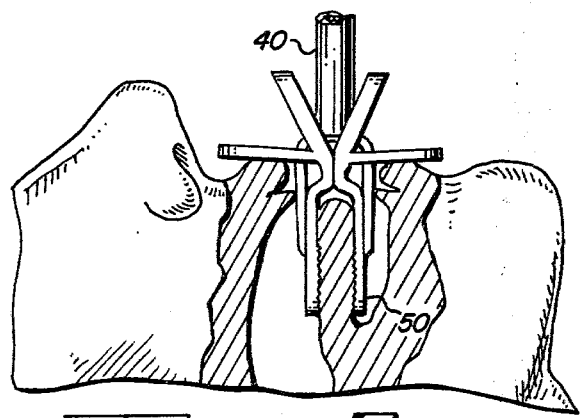
FIG. 3 is an illustration of the device of the present invention as it would appear in place inside a patient's mouth.
Figure 4:
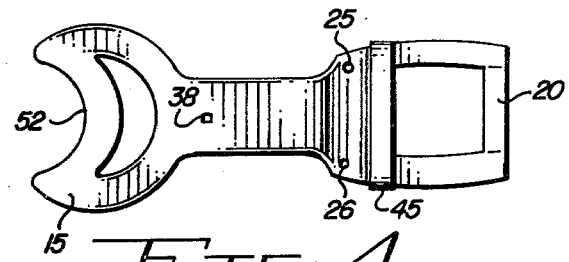
FIG. 4 is a top view of a portion of the device of FIG. 2.
Figure 5:
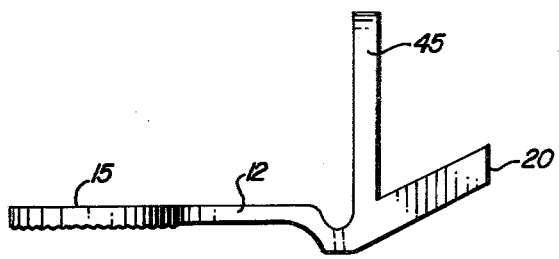
FIG. 5 is a side elevational view of the portion of the device of the present invention shown in FIG. 4.
Figure 6:
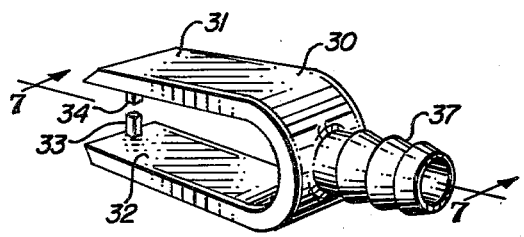
FIG. 6 is a perspective view of the spring and integral tubular extension of the device of the present invention.
Figure 7:
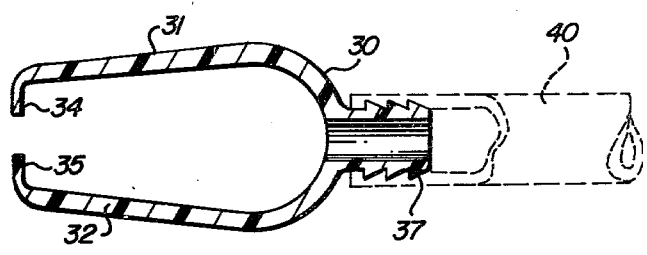
FIG. 7 is a cross-sectional view of FIG. 6 taken along lines 7—7.
Figure 8:
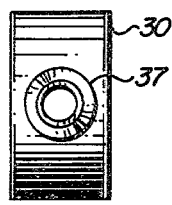
FIG. 8 is an end view of the spring and tubular extension shown in FIG. 6.

An upper stop 45 and a lower stop 46 are formed integrally with the upper clamping arm 12 and lower clamping arm 14, respectively. The stops 45 and 46 extend substantially transversely of the respective clamping arms and are positioned rearwardly of the clamps 15 and 17. In this manner, when the clamps grasp the tongue, and the forward or distal end of the apparatus 10 is pulled into the mouth by the weight of the tongue, the stops 45 and 46 contact the outside of the mouth as shown in FIG. 3 to limit the distance that the apparatus may be pulled into the mouth. In the embodiment chosen for illustration, the upper clamping arm 12 and the lower clamping arm 14 are identical and the clamps 15 and 17 are also identical; therefore, it is of no importance whether the upper clamping arm is positioned near the roof of the mouth or the floor of the mouth. However, to permit the respective clamps 15 and 17 to grasp the tongue without interference from the membrane extending from the floor of the mouth to the interior surface of the tongue, or frenulum of the tongue 50, both of the clamps 15 and 17 are provided with indented portions such as that shown at 52. Thus, the clamp may conveniently be placed underneath the tongue while the opposing clamp is placed on top of the tongue without interference.

The apparatus of the present invention operates as follows. The upper and lower grips 20 and 22 are grasped and force is applied causing the two to approach each other, which in turn, causes relative pivoting between the upper and lower clamping arms 12 and 14 about the fulcrum 19. The two clamping arms are prevented from sliding motion with respect to each other by the two pivot pins 25 and 26. The spring 30 is thus forced apart by the motion of the clamping arms 12 and 14 and the device is then positioned on the tongue with the clamps 15 and 17 in contact with the upper and lower surfaces of the tongue. The indented portion of the lower clamp prevents interference between the clamp and the frenulum of the tongue. Pressure is then released from the upper and lower grips 20 and 22 to thereby permit the spring arms 31 and 32 to force the clamps 15 and 17 toward each other to thereby grip the tongue. The tongue is thus firmly grasped and the apparatus is permitted only limited intrusion into the mouth through the expediency of the upper and lower stops 45 and 46 which contact the outside of the person's mouth. The tongue, thus firmly held, is prevented from receding and blocking the trachea while the apparatus also acts as a block to prevent the person's teeth from contacting and possibly injuring the tongue. The outstanding from the mouth portion of the apparatus is also small enough to permit mouth-to-mouth respiration while it is in place. In the event the administration of oxygen or other gases is indicated, the tubular extension 37 is conveniently positioned for attachment to a hose. The device is sufficiently inexpensive to permit sterile prepackaging with subsequent disposability.

It will be obvious to those skilled in the art that many modifications may be made in the embodiment chosen for illustration without departing from the scope of the invention. For example, the upper and lower clamping arms may be secured against relative sliding movement at the fulcrum thereof by other than stainless steel stake pins 25 and 26 as shown. In the embodiment chosen for illustration, the upper and lower clamping arms are identical so that a single mold may be utilized to produce both arms; however, the stake pins 25 and 26 could be replaced by simply molding the upper arm with pins extending therefrom and the lower arm with detents or holes to receive the extensions from the upper arm.

I claim:

1. Apparatus for grasping and holding a tongue to prevent the tongue from obstructing the trachea comprising:
   (a) an upper and a lower clamp arm each having a first surface opposing the other and each having a second surface facing away from the other;
   (b) an upper and lower clamp each secured at a distal end of said upper and lower clamp arm, respectively, for grasping and holding the tongue of an unconscious person, said clamps each including an indented portion to prevent said clamps, when in position in the person's mouth, from contacting the frenulum of the tongue;
   (c) said clamp arms including stop means formed integrally therewith extending substantially transversely to said arms at a position rearwardly of said clamp for contacting the outside of the person's mouth;
   (d) U-shaped spring means contacting each of said clamp arms on said second surface to urge said upper and lower clamp arms toward each other and to force said arms into rocking contact with each other; and
   (e) said U-shaped spring means including a tubular extension for attachment to a flexible hose to supply a selected gas to said person.

2. The combination set forth in claim 1 including an upper and a lower grip each secured to a proximal end of a different one of said clamp arms, said tubular extension extending between said grip.

3. The combination set forth in claim 1 wherein said upper clamp, upper clamp arm, upper grip, and upper stop are integrally formed from a single unitary piece of rigid material, and wherein said lower clamp, lower clamp arm, lower grip and lower stop are integrally formed from a second single unitary piece of rigid material.

4. The combination set forth in claim 3 wherein said rigid material is molded plastic.

* * * * *